United States Patent
Zimmerman

(10) Patent No.: US 10,966,410 B2
(45) Date of Patent: Apr. 6, 2021

(54) THERAPEUTIC DEVICE FOR HEATING AND ICING BODY PARTS

(71) Applicant: Z DESIGN, INC., Denver, CO (US)

(72) Inventor: Cary D. Zimmerman, Denver, CO (US)

(73) Assignee: Z DESIGN, INC., Denver, CO (US)

(*) Notice: Subject to any disclaimer, the term of this patent is extended or adjusted under 35 U.S.C. 154(b) by 394 days.

(21) Appl. No.: 15/902,457

(22) Filed: Feb. 22, 2018

(65) Prior Publication Data

US 2018/0242555 A1      Aug. 30, 2018

Related U.S. Application Data

(60) Provisional application No. 62/463,278, filed on Feb. 24, 2017.

(51) Int. Cl.
| | | |
|---|---|---|
| *A01K 13/00* | (2006.01) | |
| *A61D 9/00* | (2006.01) | |
| *A61F 7/02* | (2006.01) | |

(52) U.S. Cl.
CPC .............. *A01K 13/006* (2013.01); *A61D 9/00* (2013.01); *A61F 7/02* (2013.01); *A61F 2007/023* (2013.01); *A61F 2007/0225* (2013.01); *A61F 2007/0228* (2013.01); *A61F 2007/0268* (2013.01); *A61F 2007/0279* (2013.01)

(58) Field of Classification Search
CPC combination set(s) only.
See application file for complete search history.

(56) References Cited

U.S. PATENT DOCUMENTS

| | | | |
|---|---|---|---|
| 2,518,373 A | 8/1950 | Reeves | |
| 2,955,044 A | 10/1960 | Tupper | |
| 3,804,077 A * | 4/1974 | Williams | ................. A61F 7/03 |
| | | | 126/263.1 |
| 4,479,457 A | 10/1984 | Rotolo | |
| 4,585,003 A | 4/1986 | Meistrell | |
| 4,586,506 A | 5/1986 | Nangle | |
| 4,688,572 A | 8/1987 | Hubbard et al. | |
| 5,072,598 A | 2/1991 | Dibrell | |
| 5,020,711 A | 6/1991 | Kelley | |
| 5,069,208 A | 12/1991 | Noppel et al. | |

(Continued)

FOREIGN PATENT DOCUMENTS

| | | |
|---|---|---|
| FR | 1365666 | 12/1964 |
| WO | WO 2016/198904 | 12/2016 |

OTHER PUBLICATIONS

"Bella's Hot/Cold Pain Relief Pack for dogs," BellasPainRelief. com, as of Feb. 12, 2016, 3 pages [retrieved online on Feb. 12, 2016 from: www.bellaspainrelief.com].

(Continued)

*Primary Examiner* — Joseph A Stoklosa
*Assistant Examiner* — Adam J Avigan
(74) *Attorney, Agent, or Firm* — Sheridan Ross P.C.

(57) ABSTRACT

Systems and methods for treating and rehabilitating animals are provided. The systems and methods include harnesses and related devices, including compresses and heating/icing devices. The devices further include and comprise features to enable the device to be contoured to and secured to an animal. Animals contemplated for use with devices and methods of the present disclosure include, but are not limited to, canines and humans.

20 Claims, 13 Drawing Sheets

(56) References Cited

U.S. PATENT DOCUMENTS

| | | |
|---|---|---|
| 5,137,508 A | 8/1992 | Engman |
| 5,148,804 A | 9/1992 | Hill et al. |
| 5,152,285 A | 10/1992 | Gnegy |
| 5,466,251 A | 11/1995 | Brunson et al. |
| 5,496,358 A | 3/1996 | Rosenwald |
| 5,537,954 A | 7/1996 | Beeghly et al. |
| 5,984,953 A | 11/1999 | Sabin et al. |
| 6,086,609 A | 7/2000 | Buckley |
| 6,099,555 A | 8/2000 | Sabin |
| 6,240,882 B1 | 6/2001 | Gross |
| 6,598,235 B2 | 7/2003 | Bulla |
| D653,411 S | 1/2012 | Elliott |
| 8,683,764 B2 | 4/2014 | Smith et al. |
| 2004/0244413 A1 | 12/2004 | Trinh et al. |
| 2005/0284416 A1 | 12/2005 | Smit et al. |
| 2006/0213156 A1 | 9/2006 | Nilfuroshan |
| 2007/0204808 A1 | 9/2007 | Harada |
| 2009/0222071 A1 | 9/2009 | Li et al. |
| 2010/0161015 A1 | 6/2010 | Wilson et al. |
| 2013/0041440 A1 | 2/2013 | Kingsley |
| 2014/0058486 A1 | 2/2014 | Moore, Jr. |
| 2015/0045859 A1 | 2/2015 | Kay |
| 2016/0030238 A1* | 2/2016 | Foster ................ A61F 7/02 607/110 |

OTHER PUBLICATIONS

"Canine Icer—Stifle," Clean Run, as of Feb. 12, 2016, 2 pages [retrieved Feb. 12, 2016 online from: www.cleanrun.com/index.cfm?fuseaction=product.display&product_ID=2219&ParentCat=400].

International Search Report and Written Opinion for International (PCT) Patent Application No. PCT/US18/19165, dated May 4, 2018 7 pages.

International Preliminary Report on Patentability for International (PCT) Application No. PCT/US18/19165, dated Sep. 6, 2019, 6 pages.

Official Action for Australian Patent Application No. 2018224086, dated Jun. 29, 2020, 5 pages.

Extended European Search Report for European Patent Application No. 18756639, dated Nov. 19, 2020, 8 pages.

* cited by examiner

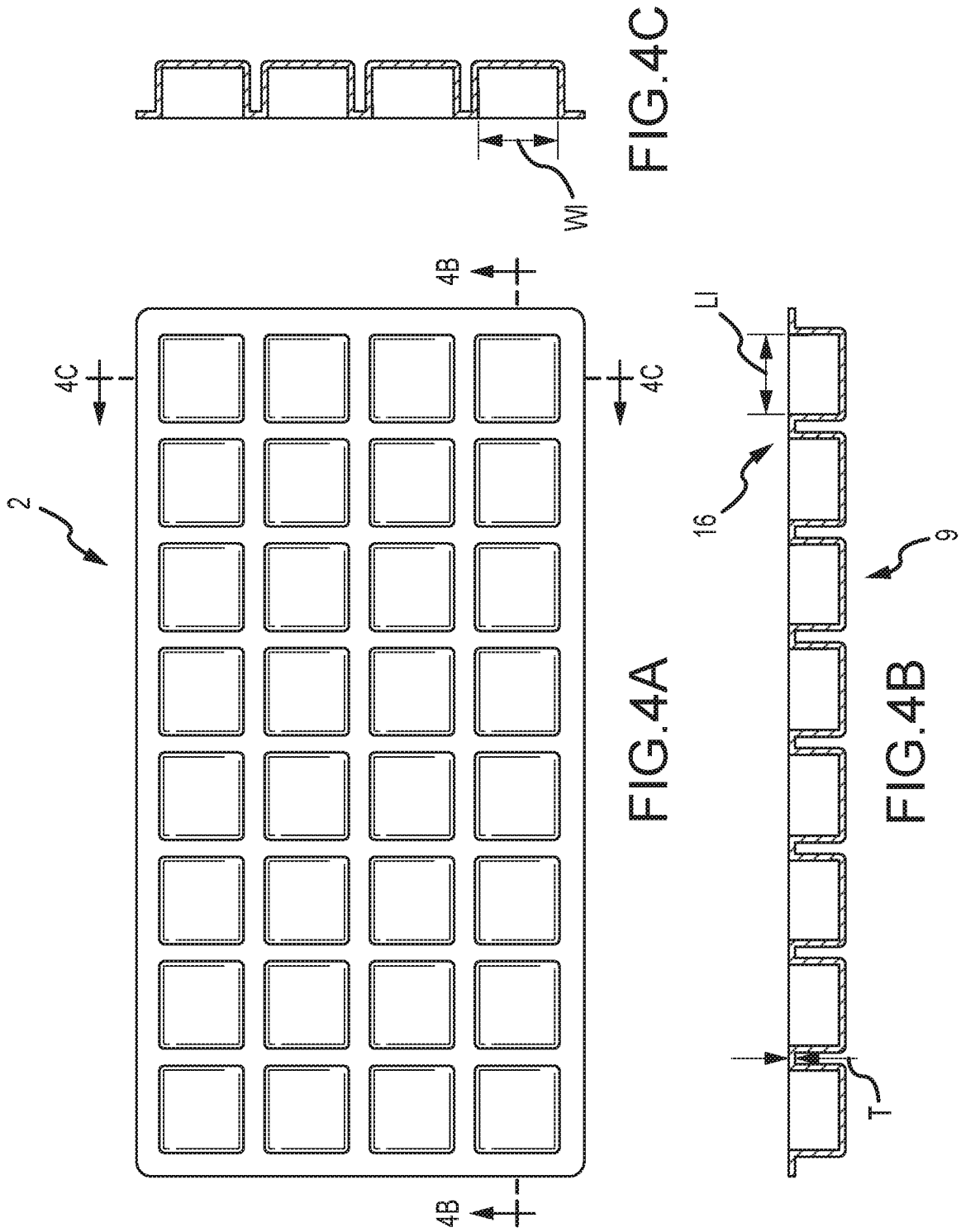

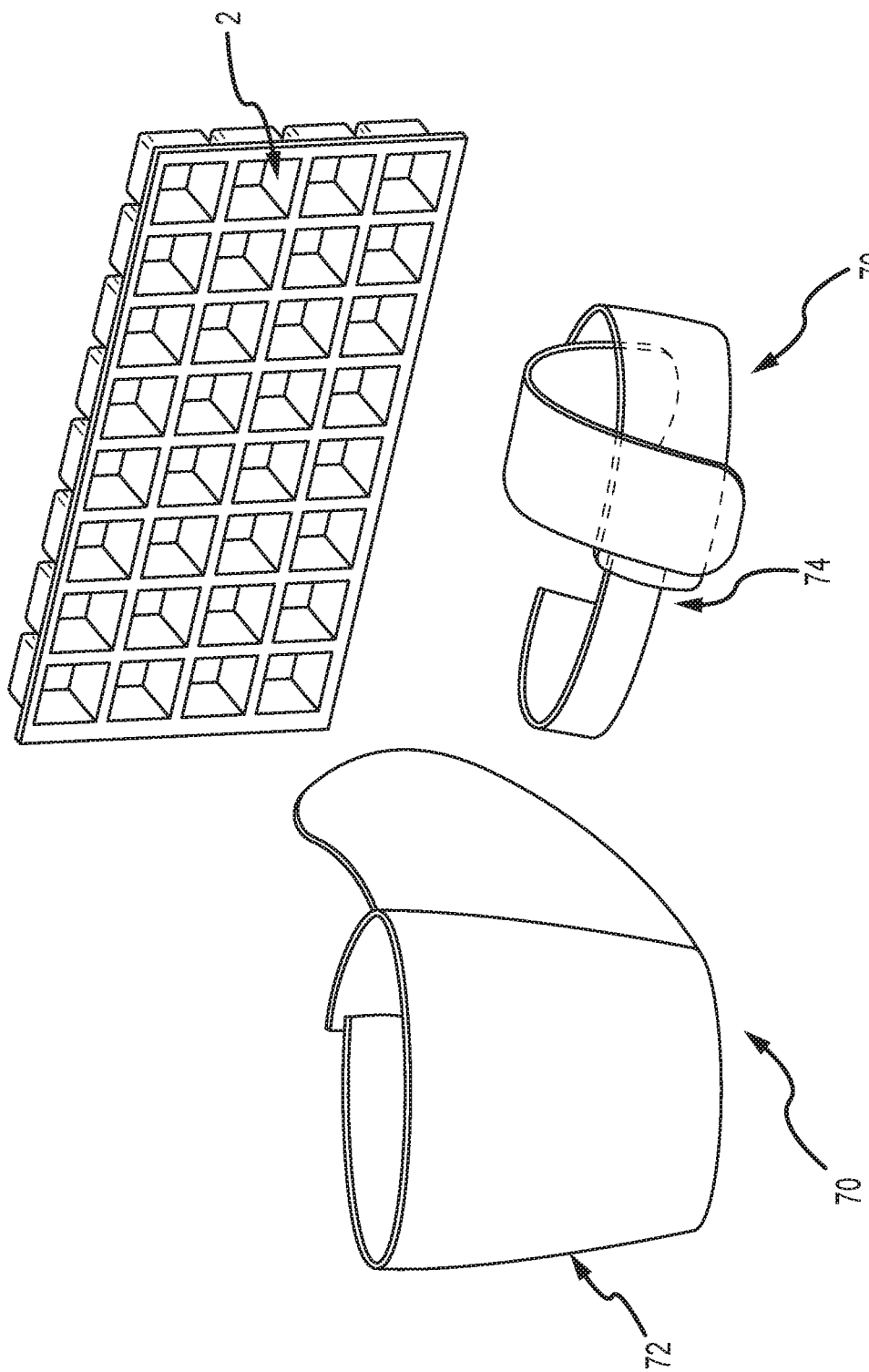

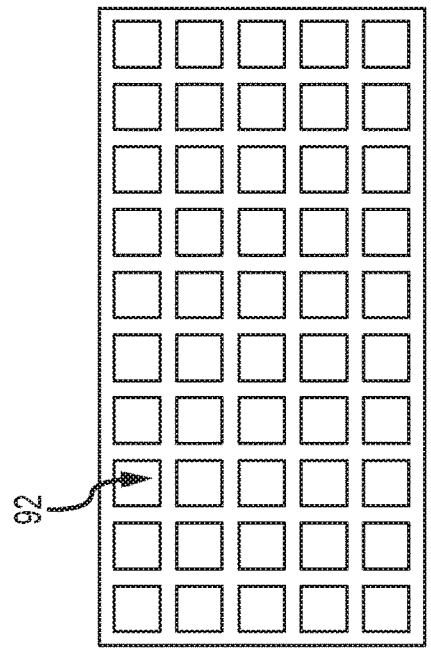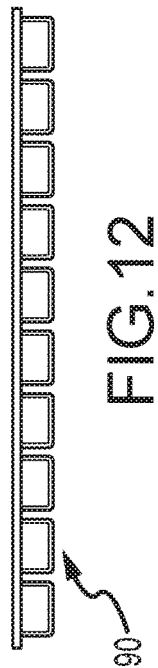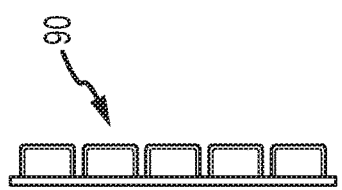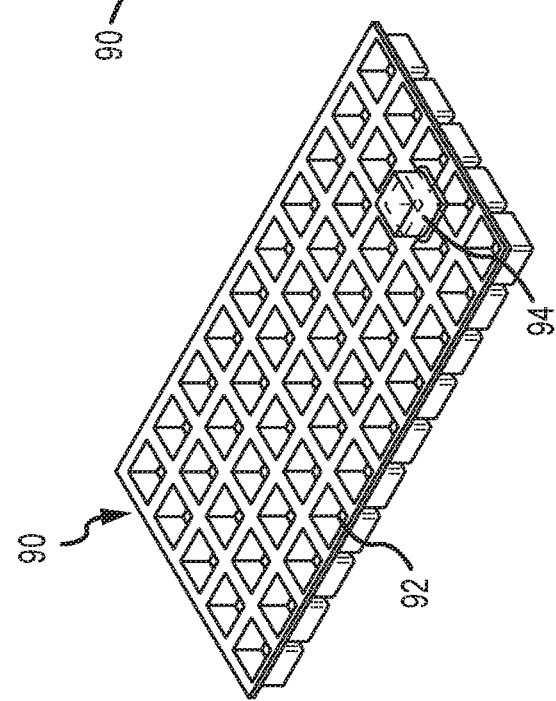

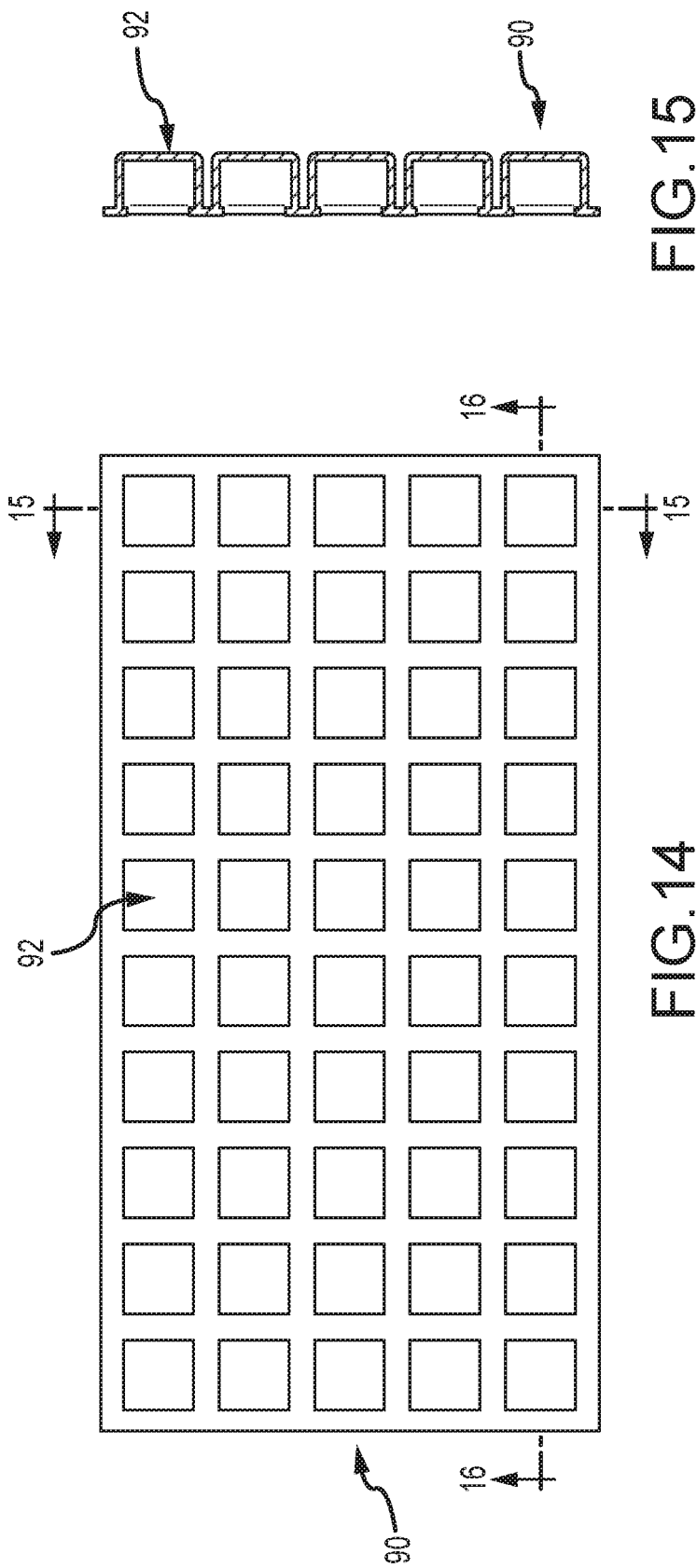

THERAPEUTIC DEVICE FOR HEATING AND ICING BODY PARTS

This U.S. Non-Provisional Patent Application claims the benefit of priority from U.S. Provisional Patent Application Ser. No. 62/463,278, filed Feb. 24, 2017, the entire disclosure of which is hereby incorporated by reference.

FIELD OF THE INVENTION

The present disclosure relates to methods and devices for treating animals. More specifically, embodiments of the present disclosure comprise methods and devices for applying treatment to animals and assisting animals with mobility and other functions.

BACKGROUND OF THE INVENTION

As dogs and other pets begin to age so do their limbs, joints and muscles. It is not uncommon for animals to develop arthritis in their joints, specifically their hips or shoulders. Activities that were once easy for an animal to participate in become difficult or impossible. One of the most difficult activities for an animal suffering from these conditions is for them to get up after sitting down. Other activities that become cumbersome are walking up and down stairs, going for a daily walk, or entering and exiting a vehicle.

Animals including, but not limited to, dogs undergo procedures and surgeries which are known to cause injury to the animal and require rehabilitation. This rehabilitation may include, for example, a need to apply a hot or cold compress to a portion of the animal. The body geometry or certain animals the animal's general lack of understanding of such processes poses various complications for applying ice packs, compresses, etc. Even well-behaved animals are not likely to remain immobile while a cold-compress is applied to a particular portion of the animal's anatomy.

Additionally, animals recovering from injury or surgery, and animals dealing with physical impairments may require mobility assistance. For example, animals may require support or assistance while performing basic functions related to walking and/or may require support, assistance, restraint, or guidance while performing specific rehabilitation tasks such as hydrotherapy.

SUMMARY OF THE INVENTION

There has been a long-felt and unmet need to provide a system and method for performing various therapeutic and rehabilitative tasks with an animal. Such tasks include, for example, applying ice or cold-compresses to reduce swelling in an animal and supporting an animal during various therapeutic physical activities.

In various embodiments, a reusable compress or "ice pack" is provided that is operable for use with animals. Such animals include, but are not limited to, canines. Compresses of the present disclosure comprise features and structure that enable the device to be formed or fit to a particular area to which the device is to be applied, maintain temperature within at least a portion of the compress, and be secured to an irregularly shaped animal in a manner that reduces the risk of detachment or separation between the animal and the compress.

In some embodiments, it is contemplated that therapeutic device is operable to be provided with or is provided in combination with an attachment member. Attachment members of the present disclosure include but are not limited to harnesses as shown and described herein. However, in various embodiments, a therapeutic device is provided that does not comprise a harness or attachment member. Therapeutic devices of the present disclosure are contemplated as comprising a compress or "ice pack" in isolation and as shown and described herein.

In certain embodiments, an animal restraint and support device is provided that comprises features which are operable to receive and support a compress. Such devices also promote and enable a temperature exchange between a compress and the animal, wherein the animal and the compress are not isolated or insulated from each other. In certain embodiments, a harness is provided that comprises a receptacle or area for receiving and storing a compress in close proximity to an animal's body. In certain embodiments, a mesh layer or similarly thermally-conductive layer is provided between the compress and the animal's body to maximize heat transfer between the animal and the cold or hot compress.

In various embodiments, systems and methods are provided for securing a device to an animal, and wherein components for securing the device as well as the device itself are useful for and operable to support and/or guide an animal. In certain embodiments, an animal mobility device is provided that is operable for use with and particularly well adapted for performing hydrotherapy with an animal. Hydrotherapy, at least as used herein, relates to a method of rehabilitating or treating an animal by partially submerging the animal in a volume of water and causing or encouraging the animal to walk or swim. Frequently, hydrotherapy methods and devices comprise a treadmill wherein the animal remains relatively stationary in a volume of water while "walking" on a treadmill. Such devices generally fail to provide adequate restraint and support devices, which increases risk of injury and even drowning.

In various embodiments, a therapeutic device for treating animals is provided. Therapeutic devices of the present disclosure include, but are not limited to, hot and cold compresses which may generally be referred to herein as "compresses". It will be recognized that compress devices of the present disclosure may be particularly well adapted to be frozen or cooled and used to "ice" a body part. However, no limitation with respect to the intended use or intended temperature of such devices is provided. One of skill in the art will understand that an intended use and desired temperature of the device may simply be a product of a user's intentions. Accordingly, even though devices may be referred to herein as an "ice pack", a "cold compress", a "compress", and/or a "heating pack", no limitation with respect to the intended use of such devices is provided.

In various embodiments, a compress is provided that comprises a silicone rubber, and wherein the compress is flexible such that it may be wrapped or otherwise provided around an irregularly shaped animal body part. Compresses of the present disclosure comprise a rubber or similarly flexible housing. The housing comprises a plurality of discrete wells that store a quantity of fluid. The fluid is operable to be frozen or heated, and the compress is thereafter applied to an animal. Although various devices and methods of the present disclosure contemplate that a compress is used for therapeutic reasons in the treatment of injured or recovering animals, it is also contemplated that methods, systems and devices of the present disclosure may be used to heat or cool an animal. For example, it is contemplated that harnesses and compresses of the present disclosure may be utilized to apply ice to an animal to prevent the animal from overheating in hot weather and/or during physical activity.

In one embodiment, a harness device is provided that comprises a chest member having an upper portion and a lower portion selectively secured to the upper portion. At least one strap is provided that is adapted to be encircled around a portion of an animal. The harness further comprises a hip member having an upper portion; a lower portion, and at least one strap adapted to be encircled around a portion of the animal. A first handle is connected to the chest member, wherein the first handle has a first attaching portion, a second attaching portion, and a continuous length of material therebetween. The first handle and the second handle are adapted to receive the hand of a human for applying an upward force on at least one of the chest member and the hip member. At least one of the chest member and the hip member comprise a receptacle operable to receive a therapeutic device, and a therapeutic device is provided within and selectively removable from the receptacle. In preferred embodiments, a therapeutic device comprises a flexible silicone rubber device having a plurality of sealed wells and wherein each of the wells comprise an internal volume for storing a liquid. U.S. Pat. No. 9,320,260 to Zimmerman, which is hereby incorporated by reference in its entirety, discloses harnesses and related features that are contemplated for use with embodiments of the present disclosure. Such harnesses and features thereof may be combined with and/or provided with therapeutic compress devices of the present disclosure.

In various embodiments, harnesses devices are provided that are operable to receive and store a compress device. In preferred embodiments, harnesses comprise at least one receptacle or compress-storage means to receive, house, and store a compress in a manner wherein the compress is provided in close proximity to an animal body part that is to be subject to heat transfer with the compress device. In one embodiment, a harness is provided with at least one compress-receiving receptacle and wherein the receptacle comprises a non-insulated layer. Non-insulated layers of the present disclosure include, for example, layers of mesh or thin-fabric material that are operable to hold or support a compress, but generally do not impede or obstruct heat transfer between a compress and an animal. In some embodiments, harnesses are provided with a plurality of compress-storage means. For example, in certain embodiments, it is contemplated that a plurality of receptacles are provided on a harness and wherein each of the receptacles are adapted to receive and house a compress device. The plurality of receptacles are provided in specific locations distributed along an area of the harness. For example, it is contemplated that the receptacles are provided in an area of the harness corresponding to a shoulder, hip, pelvis, groin, and/or knee joint, as such areas are known to be generally more prone to injury than other areas of an animal's body.

In one embodiment, a harness for an animal is provided wherein the harness comprises a chest member having an upper portion; a lower portion selectively secured to said upper portion; and at least one strap adapted to be encircled around a portion of a canine. A hip member is provided that comprises an upper portion; a lower portion; and at least one strap adapted to be encircled around a portion of said animal. A first handle is connected to said chest member, wherein said first handle has a first attaching portion, a second attaching portion, and a continuous length of material therebetween. The first handle and said second handle are adapted to receive the hand of a human for applying an upward force on at least one of said chest member and said hip member. At least one of the chest member and the hip member comprises a receptacle operable to receive a therapeutic device. A therapeutic device is provided within and selectively removable from the receptacle, wherein the therapeutic device comprises a flexible silicone rubber device having a plurality of sealed wells and wherein each of said wells comprise an internal volume for storing a liquid.

In some embodiments, a compress-receiving device is provided that is selectively securable to an animal at a plurality of different locations on the animal. For example, in one embodiment, a sleeve is provided that is selectively securable to an animal by a fastener. Fasteners of the present disclosure include, for example, straps with securing means such as hook-and-loop closures, snaps, buckles, etc. The sleeve may be provided and secured to an animal at various different locations, depending upon treatment needs. For example, sleeves of the present disclosure may be wrapped and/or secured around the forearm, wrist, lower thigh, stifle, or hock of a canine. Such areas are known to be difficult to treat, as animals and particularly canines tend not to tolerate treatment or remain still for long enough for such treatment to be effective. Devices of the present disclosure provide means and methods for securing at least one compress to various different portions of an animal.

In some embodiments, the present disclosure provides a compress that is specifically designed to fit a particular anatomical part of an animal. For example, in one embodiment, an elongate sleeve member is provided that is operable to be provided over and surround a leg of an animal. The sleeve comprises sidewalls and an interior volume provided therein. The interior volume comprises at least one fluid that is operable to be frozen or heated to provide therapeutic treatment to an animal as may be desired. The sleeve preferably comprises a strap or other securing means to tighten or secure the sleeve to an animal.

In one embodiment, a therapeutic device for an animal is provided that comprises a flexible compress member having a plurality of wells. Each of the plurality of wells comprises a plurality of sidewalls and a bottom portion. Each of the plurality of wells comprises a first internal volume and an upper end of the wells comprises an overhang. A plurality of fluid-containing modules is provided, and each of the plurality of fluid-containing modules is operable to be provided within the first internal volume of a well. Each of the fluid-containing modules comprises a substantially rectangular cube having an upper end, a lower end, a plurality of sidewalls and a second internal volume, the second internal volume being less than the first internal volume. A fluid is provided within the second internal volume. The overhang comprises at least one of a flexible and an elastic component that is operable to selectively receive and at least partially secure a portion of a fluid-containing module. The device is operable to act as a heating or cooling agent for an animal body part.

In another embodiment, a therapeutic device for an animal is provided that comprises a flexible compress member having a plurality of wells. Each of the plurality of wells comprises a first internal volume and an upper end of the wells comprises an overhang. A plurality of fluid-containing modules, wherein each of the plurality of fluid-containing modules is operable to be provided within the first internal volume of a well. Each of the fluid-containing modules comprise a second internal volume, the second internal volume being less than the first internal volume. A fluid is provided within the second internal volume. The overhang comprises at least one of a flexible and an elastic component that is operable to selectively receive and at least partially secure a portion of a fluid-containing module. The device is operable to act as a heating or cooling agent for an animal body part.

In another embodiment, a therapeutic device for an animal is provided that comprises a flexible member having a plurality of wells. Each of the plurality of wells comprises a plurality of sidewalls and a bottom portion. Each of the plurality of wells comprises a first internal volume. A plurality of fluid-containing modules are provided, wherein each of the plurality of fluid-containing modules is operable to be provided within a well. Each of the fluid-containing modules comprises a substantially rectangular cube having an upper end, a lower end, a plurality of sidewalls and a second internal volume, the second internal volume being less than the first internal volume. A fluid is provided within the second internal volume. The wells comprise at least one of a flexible and an elastic component that is operable to selectively receive and at least partially secure a portion of a fluid-containing module. The device is operable to act as a heating or cooling agent for an animal body part.

In various embodiments, fluid-containing modules of the present disclosure comprises substantially rectangular cubes. As used herein, substantially rectangular cubes and cubical structures include, but are not limited to, cubes, cubes with one or more rounded corners, cubes with indentation or impressions in one or more sidewalls, square cubes, elongate rectangular cubes, and similar structures. It will be recognized that various different geometric and polygonal shapes are within the scope and spirit of the invention, and no limitation is provided with respect to the exact shape(s) of the fluid-containing modules. In some embodiments, it is contemplated that fluid-containing modules comprise spherical or ovoid shaped modules. In such embodiments, the wells of a device comprise a corresponding shape to receive the spherical or ovoid modules.

This Summary is neither intended or should it be construed as being representative of the full extent and scope of the present invention. The present invention is set forth in various levels of detail and the Summary as well as in the attached drawings and in the detailed description of the invention and no limitation as to the scope of the present invention is intended by either the inclusion or non-inclusion of elements, components, etc. in the Summary. Additional aspects of the present invention will become more readily apparent from the detailed description, particularly when taken together with the drawings.

BRIEF DESCRIPTION OF THE DRAWINGS

The accompanying drawings which are incorporated herein and constitute a part of the specification, illustrate various embodiments of numerous inventions and together with the general description of the invention given provide the detailed description, and the drawings serve to explain the principles of these embodiments.

FIG. 4A is a top plan view of a therapeutic device according to one embodiment of the present disclosure.

FIG. 4B is a cross-sectional elevation view of a therapeutic device according to one embodiment of the present disclosure.

FIG. 4C is a cross-sectional elevation view of a therapeutic device according to one embodiment of the present disclosure.

FIG. 8 is a perspective view of a therapeutic device according to one embodiment of the present disclosure.

FIG. 10 is a perspective view of therapeutic device according to one embodiment of the present disclosure.

FIG. 11 is a top plan view of the therapeutic device according to the embodiment of FIG. 10.

FIG. 12 is a side elevation view of the therapeutic device according to the embodiment of FIG. 10.

FIG. 13 is a side elevation view of the therapeutic device according to the embodiment of FIG. 10.

FIG. 14 is a top plan view of the therapeutic device according to the embodiment of FIG. 10.

FIG. 15 is a side elevation view of the therapeutic device according to the embodiment of FIG. 10.

FIG. 16 is a side elevation view of the therapeutic device according to the embodiment of FIG. 10.

It should be understood that the drawings are not necessarily to scale. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION

Figure 1:
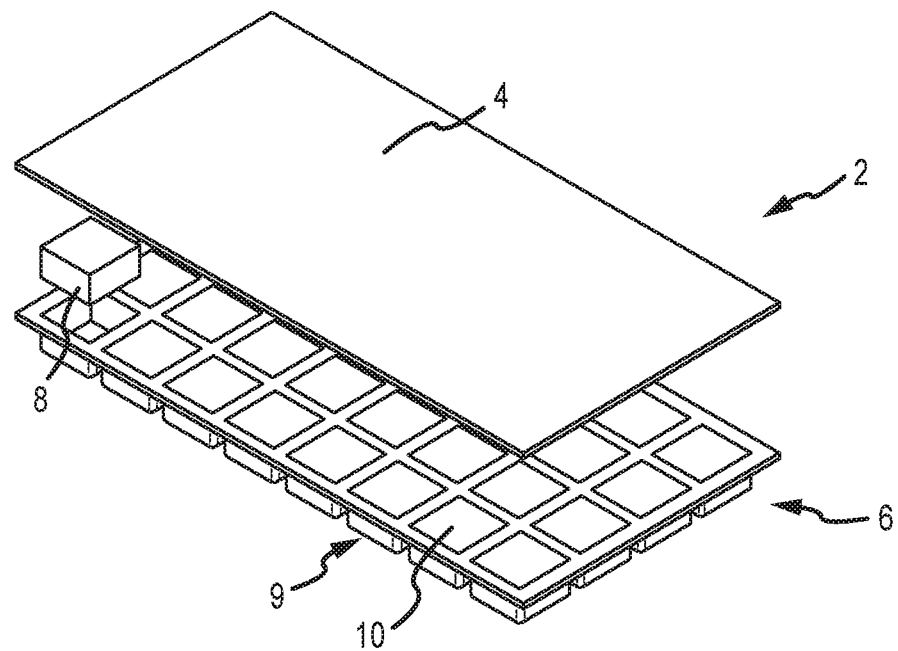
FIG. 1 is an exploded perspective view of a therapeutic device according to one embodiment of the present disclosure.

FIG. 1 is an exploded perspective view of a compress device 2 according to one embodiment of the present disclosure. As shown, the device 2 of FIG. 1 comprises a compress device adapted for use with animals. The device 2 comprises a cover member 4 comprising a cover or seal, a lower portion 6, and a plurality of wells 9. The wells 9 comprise an internal volume 8 for storing a liquid 10. The entire device 2, including the liquid 10 is intended to be placed in a freezer or otherwise chilled to cool or freeze the liquid 10 provided within the wells 9. The term "liquid", at least as used herein, is not limited to water or Newtonian fluids. It is contemplated that compress devices 2 of the present disclosure comprise a "gel" useful for reusable ice packs and compresses. Such "gels" include, but are not limited to various materials useful for repeated freezing and thawing and/or comprising desirable properties such as a preferred specific heat capacity. Gels for use with embodiments of the present disclosure preferably comprise non-toxic refrigerant gels such as hydroxyethyl cellulose, sodium polyacrylate, vinyl-coated silica gel, benzoic acid, hexadienoic acid, propenoic acid, propanetriol, water, and combinations thereof. Although devices of the present disclosure are contemplated for use as compresses or ice packs and are referred to herein as such, it is also contemplated that devices of the present disclosure may be heated and used to apply heat to a body part. Accordingly, the term "compress" should not be viewed as limiting devices of the present disclosure to a particular use or application. Methods and intended uses of devices shown and described herein include the application of high and low temperatures for icing or heating an animal body part.

Figure 2:
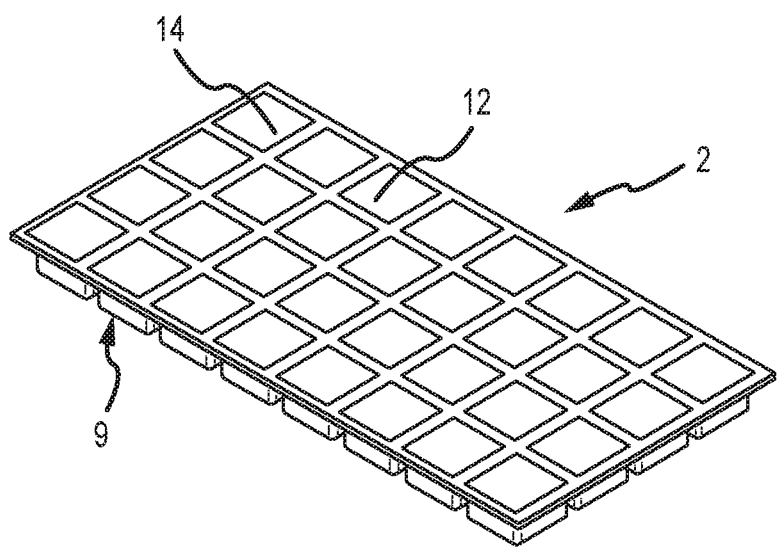
FIG. 2 is a perspective view of a therapeutic device according to one embodiment of the present disclosure.

FIG. 2 is a perspective view of the compress device 2 of FIG. 1 and provided in an assembled state. As shown, the lower portion 6 and the cover member 4 are sealingly engaged to seal and enclose the wells 9. Preferably, the cover member 4 is heat sealed and/or ultrasonically welded to the lower portion 6 and wherein the connection between the cover member 4 and the lower portion 6 comprises a permanent connection. The cover member 4 is preferably sealed along both columns 12 and rows 14 provided between and at least partially defining the wells 8. Such an arrangement provides that each of the individual wells 8 are permanently sealed to prevent leakage of liquefied contents of the wells 8.

Figure 3A:
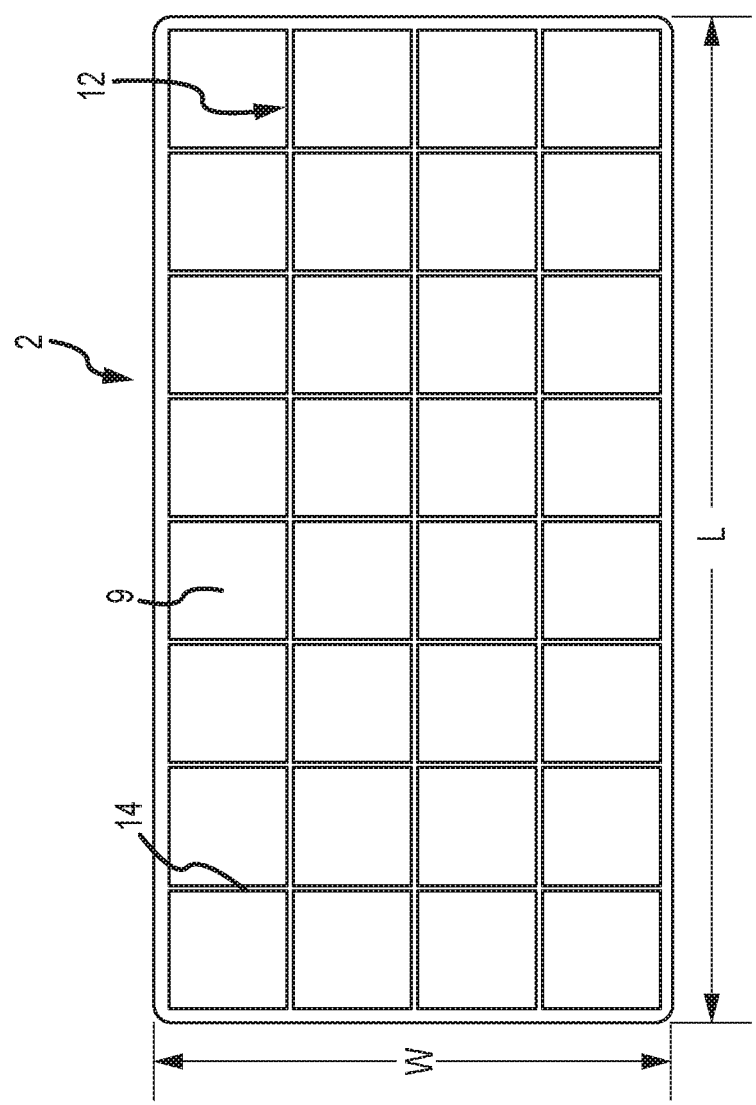
FIG. 3A is a top plan view of a therapeutic device according to one embodiment of the present disclosure.

FIG. 3A is a top plan view of a compress device 2 according to one embodiment of the present disclosure. As shown, the device 2 comprises a plurality of columns 12 and rows 14 that at least partially define a plurality of wells 9 for storing a cooling agent, such as a liquid. The device 2 of FIG. 3A comprises a 4×8 grid of wells with 32 wells 9 in total. It will be recognized, however, that compress devices of the present disclosure are not limited to this arrangement or to any specific number or pattern of wells. It is expressly contemplated that compress devices of the present disclosure may comprise any number of wells, and may also comprise different patterns and arrangements of wells. The device 2 of FIG. 3A comprises a length L and a width W. In various embodiments, the length of the device 2 comprises a length of between approximately 200 and 400 millimeters, and preferably of approximately 253 millimeters. In various embodiments, the width W of the device 2 comprises a width of between approximately 100 and 200 millimeters, and preferably of approximately 130 millimeters.

Figure 3B:
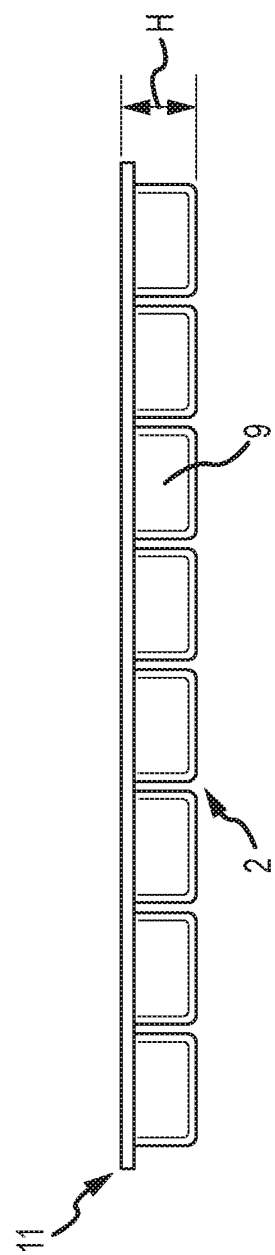
FIG. 3B is an elevation view of a therapeutic device according to one embodiment of the present disclosure.

FIG. 3B is an elevation view of the device 2 of FIG. 3A. As shown in FIG. 3B, the device 2 comprises a plurality of wells 9 extending below an upper portion of the device and wherein a height H of the device 2 extends between a bottom portion of the wells and the upper portion of the device 2. The height of the device 2 shown in FIG. 3B comprises of between approximately 10 and 30 millimeters and preferably of approximately 17.2 millimeters. The device 2 of FIG. 3B comprises a substantially flush upper surface 11. Either of the upper surface 11, or an opposing lower surface, or a combination thereof may be provided as adjacent to or proximal to an animal for therapeutic purposes.

Figure 3C:
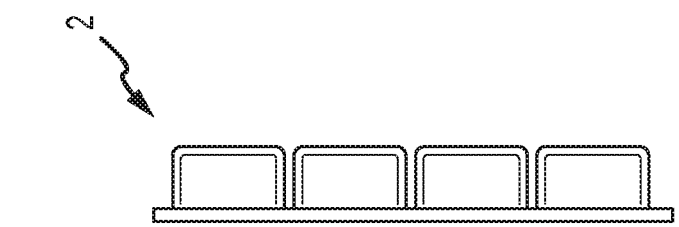
FIG. 3C is an elevation view of a therapeutic device according to one embodiment of the present disclosure.

FIG. 3C is a side elevation view of the compress device according to the embodiment of FIGS. 3A-3B. In various embodiments, and as shown in FIGS. 3B-3C, the height H of the device generally does not vary along the length L or the width W of the device 2. As shown in FIGS. 3A-3C, the wells 9 of the device 2 are spaced apart and comprise gaps therebetween. A height of the device therefore comprises some variation along the length and width due to these gaps. In general, however, a maximum height of the device 2 is determined by a distance between the bottom of the wells 9 and the upper surface 4, and this maximum height does not vary over the length or the width.

FIG. 4A is a top plan view of the device 2 according to the embodiment of FIG. 3A. FIG. 4B is a cross-sectional elevation view of the embodiment of FIG. 4A and taken at line B-B of FIG. 4A. As shown in FIG. 4B, the wells 9 comprise an interior length L1 of between approximately 15 and 40 millimeters, and preferably of approximately 25.1 millimeters. A gap space 16 is provided between each adjacent wells 9. The gap space preferably comprises a space of between approximately 2 and 10 millimeters, and preferably of approximately 5.4 millimeters. A thickness T of the columns 12 and rows 14 comprises thickness of between approximately 0.5 and 5.0 millimeters, and preferably of approximately 1.50 millimeters.

As shown in FIG. 4C, an interior of the wells 9 comprises an internal width WI that is preferably between approximately 15 and 50 millimeters, and preferably of approximately 24.5 millimeters. Wells 9 of the present disclosure therefore comprise a volume of between approximately 5.0 and 15.0 cubic centimeters. Preferably, the internal volume of the wells 9 comprises a volume of approximately 10.5 cubic centimeters.

Figure 5:
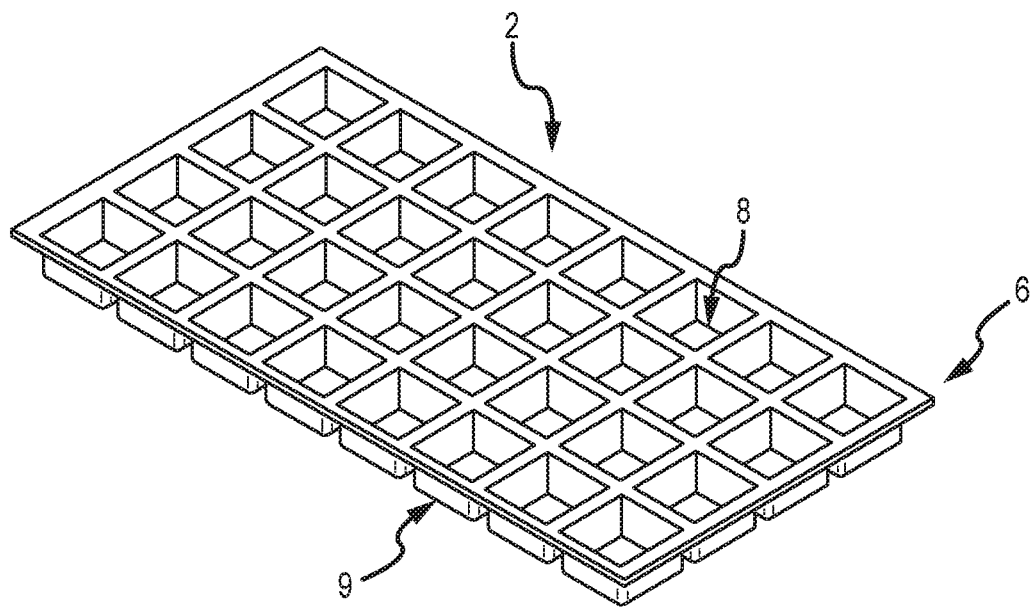
FIG. 5 is a perspective view of a therapeutic device according to one embodiment of the present disclosure.

FIG. 5 is a perspective view of a compress device 2 according to one embodiment of the present disclosure. Compress devices 2 of the present disclosure preferably comprise a silicone material wherein the device is flexible such that it may conform to an animal body part. In certain embodiments, a compress device 2 comprises a translucent silicone rubber material. The interior and/or exterior of the compress device 2 may be treated with a light electrical discharge machining finish.

Figure 6:
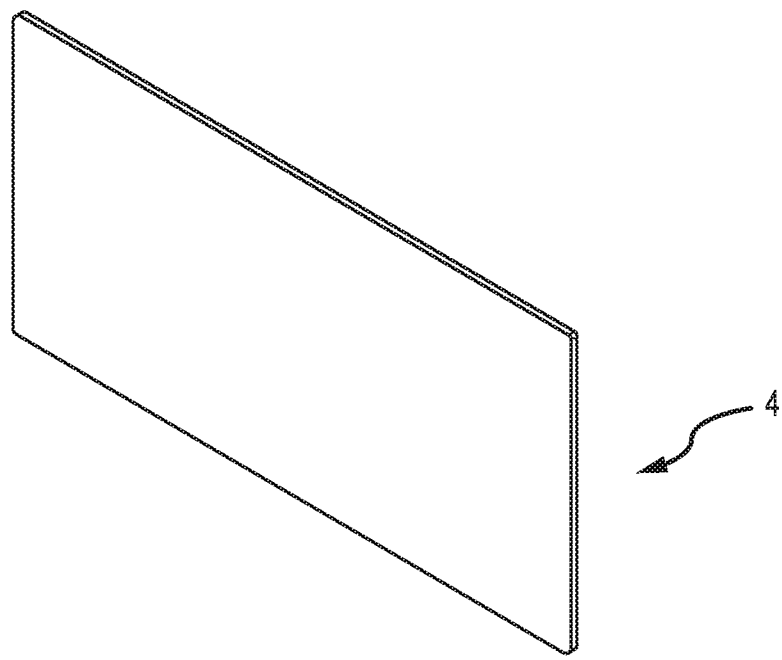
FIG. 6 is a perspective view of a component of a therapeutic device according to one embodiment of the present disclosure.
Figure 7A:
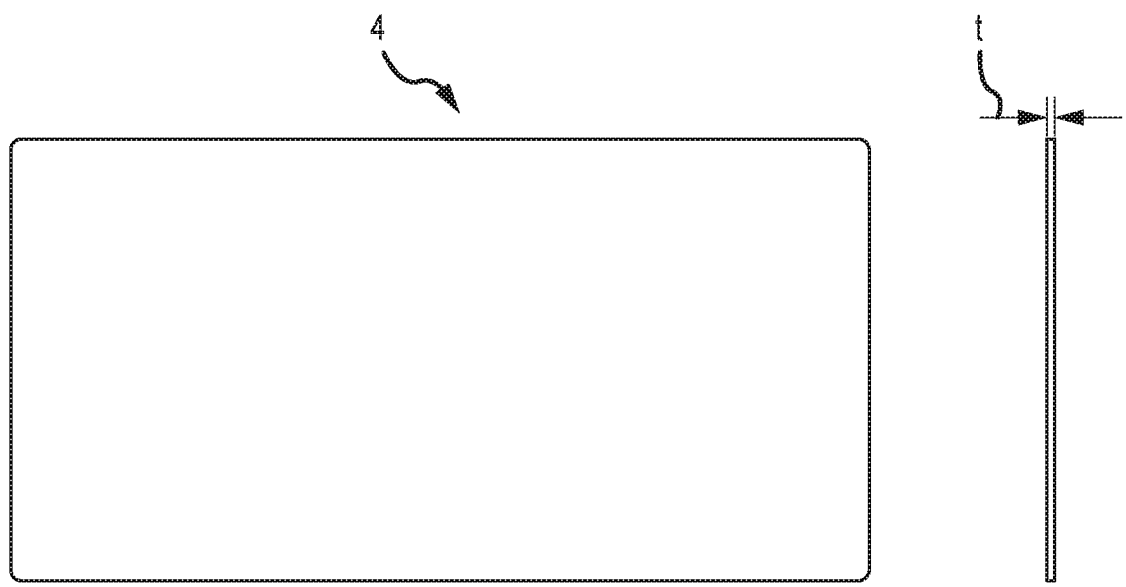
FIG. 7A is a plan view of the component of FIG. 6.
Figure 7B:
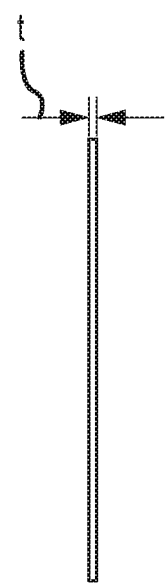
FIG. 7B is a side view of the component of FIG. 6.

FIG. 6 is a perspective view of a cover member 4 in isolation and according to one embodiment of the present disclosure. FIGS. 7A and 7B are top plan and side elevation views of the cover member 4 according to the embodiment of FIG. 6. As shown, the cover member 4 comprises a flexible silicone rubber material having a length L and a width W. The cover member 4 is adapted to be secured to a remainder of a compress device 2 as shown and described herein. The cover member 4 comprises a thickness t, wherein the thickness t is between approximately 0.50 and 5.0 millimeters, and is preferably of approximately 1.20 millimeters.

FIG. 8 is a perspective view of therapeutic devices according to certain embodiments of the present disclosure. As shown, a compress device 2 is provided. The compress device 2 comprises substantially the same device and construction as that shown with respect to FIGS. 1-5. In one embodiment, a sleeve 70 is provided to receive the compress 2 and secure the compress 2 to an animal or patient in a desired orientation. The sleeve 70 comprises a slot 72, wherein the slot 72 comprises an aperture or inlet for providing a compress 2 within the sleeve 70. The sleeve may be wrapped or contoured around a body part of an animal/ patient. In certain embodiments, portions of the sleeve 70 comprise hook-and-loop closures for securing the sleeve 70 in a desired position. FIG. 16 also provides a sleeve 70 of another embodiment wherein at least one detachable strap 74 is provided. The detachable strap 74 is selectively connected to the sleeve 70 for additional support, and is useful when securing the sleeve 70 to an animal that is unlikely to remain still or immobile during the application of ice and/or a compress.

Figure 9:
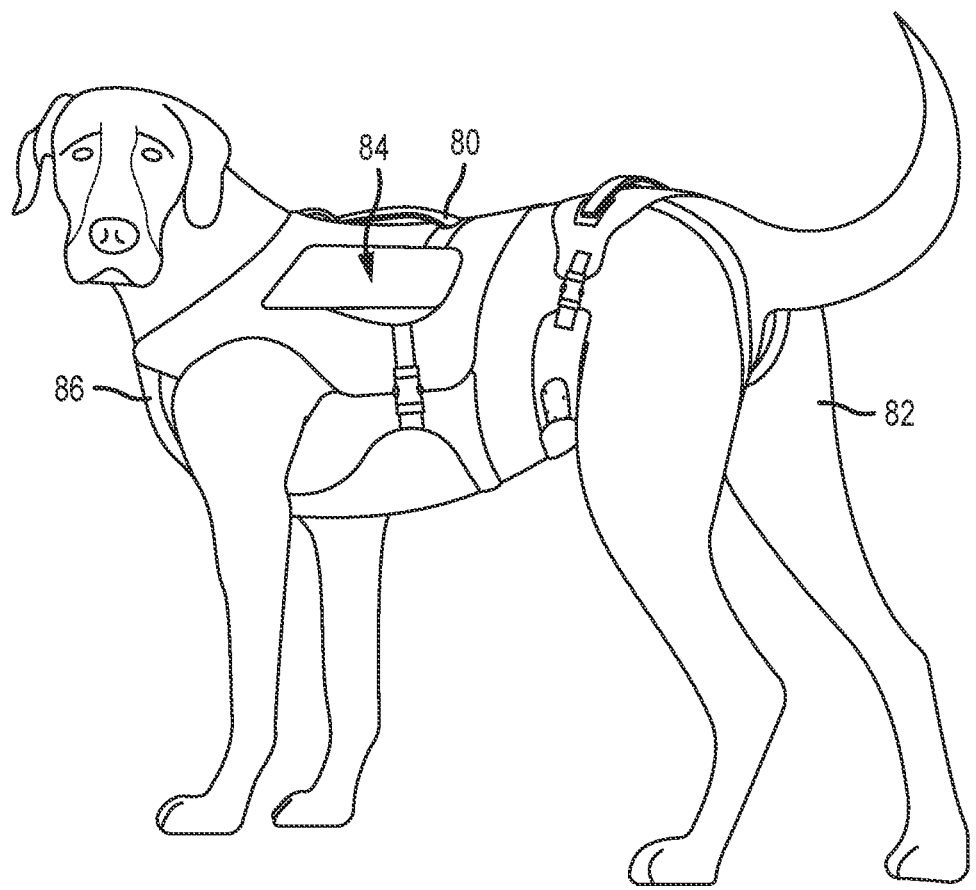
FIG. 9 is a perspective view of a therapeutic device according to one embodiment of the present disclosure.

FIG. 9 is a perspective view of a harness 80 according to one embodiment of the present disclosure. The harness 80 is provided on an animal 82 for illustrative purposes. A forward portion of the harness 80 comprises a receptacle 84 for receiving a therapeutic device, such as a compress 2. The receptacle 84 is provided in a forward portion of the harness 80 proximal to the withers of the animal 82. It will be recognized, however, that the receptacle 84 can be provided at various different locations, and that a plurality of receptacles may be provided for increasing treatment options.

The harness 80 of FIG. 9 also comprises a selectively inflatable bladder 86. The bladder 86 is provided on or proximal to a chest portion of the animal 82 and comprises a selectively sealable volume that may be filled with air to increase the buoyancy of the harness 80 and thereby convert the harness from a standard mobility assistance device to a flotation device or partial-floatation device. When inflated, the bladder 86 and associated harness 80 preferably serve to increase an animal's buoyancy 82, which is advantageous for animals when swimming or undergoing hydrotherapy procedures. Although the bladder 86 is provided on a forward/chest portion of the harness 80, it is also contemplated that the bladder 86 may be provided in alternative positions (e.g. along the dorsal and/or rear portion of the harness). It is further contemplated that a plurality of selectively inflatable bladders are provided. For example, in some embodiments, it is contemplated that a forward portion and a rearward portion of the harness each comprise at least one selectively inflatable bladder 86.

FIGS. 10-13 provide a compress device 90 according to one embodiment of the present disclosure. As shown in FIGS. 10-13, the device 90 comprises a plurality of wells 92 for receiving fluid-containing modules 94 as shown and described herein. FIGS. 14, 15 and 16 provide top, side, and end elevation views, respectively.

Figure 19:
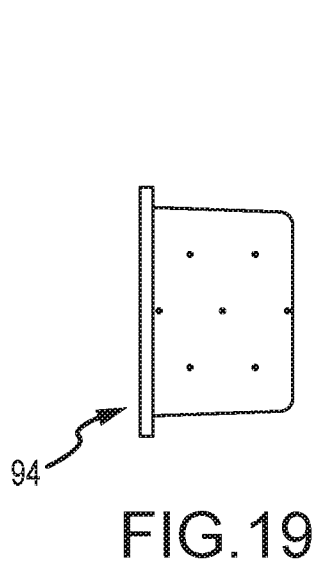
FIG. 19 is a side elevation view of the component according to the embodiment of FIG. 19.

FIG. 14 is a top plan view of the device 90 according to the embodiment of FIG. 19. FIG. 15 is a cross-sectional elevation view taken at line 15 of FIG. 14. FIG. 16 is a cross-sectional elevation view taken at line 16 of FIG. 14.

Figure 17:
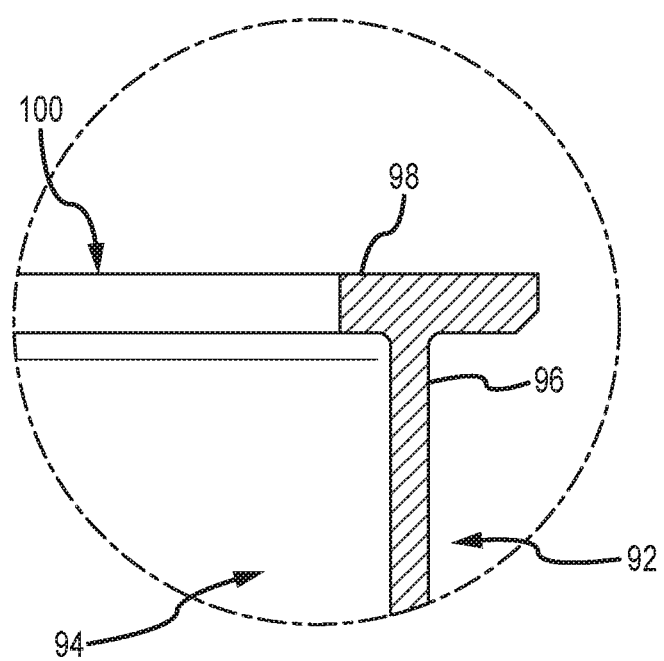
FIG. 17 is a detailed side elevation view of the device according to FIG. 10.

FIG. 17 is a detailed perspective view of the feature indicated as 17 in FIG. 16. A portion of a well 92 is shown, wherein a sidewall 96 of a well is shown, and wherein the well 92 comprises an overhang 98 and an open area 100 provided at an upper edge of the well 92. In various embodiments, the overhang 98 extends around an entire periphery of the upper end of the well. In alternative embodiments, the overhang 98 extends from only a portion of the upper end of the well (e.g. the upper edge of 3 or fewer sidewalls comprise an overhang). In various embodiments, one or more overhangs are provided to form a constriction at the upper end of the well. Overhangs and constrictions of the present disclosure comprise a feature that provide an entry of a well comprising a smaller dimension than an internal volume of the well. The well 92 is operable to receive a module 94 as shown, and wherein the overhang 98 extends over a portion of the module 94 and serves to maintain the module 94 within the volume of the well 92. The module(s) may be inserted and removed from the well 92 by way of the open end 100. Insertion and removal of the module 94 may be accomplished, for example, by bending and otherwise manipulating the flexible sidewalls of the tray 90 to insert the module 94 such that it is at least partially retained by the overhang 98 and geometry of the well 92.

Figure 18:
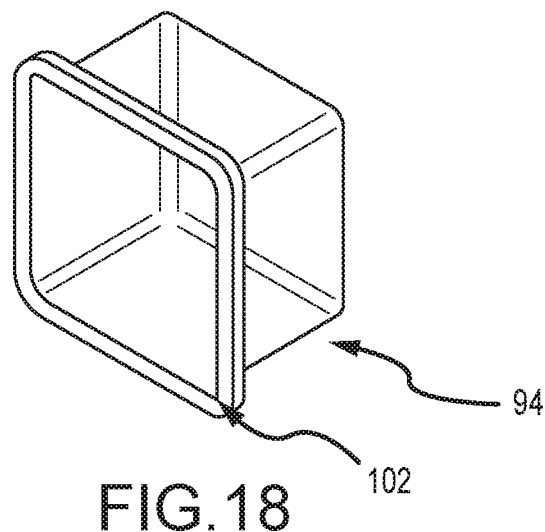
FIG. 18 is a perspective view of a component of a therapeutic device according to one embodiment of the present disclosure.

FIG. 18 is a perspective view of a module 94 according to one embodiment of the present disclosure. As shown, the module 94 comprises a silicone pod or packet that preferably comprises a predetermined quantity of fluid or gel to act as a heating or cooling agent. The modules preferably comprise an internal volume that is filled with the predetermined quantity of fluid or gel, and a sealed cover member such that the module comprise a contained and sealed quantity of fluid or gel. The cover 104 is preferably sealed by welding to the upper edges 102 of the modules 94. Thus, in certain embodiments, the modules 94 comprise sealed elements that contain a fluid or gel and which may be selectively inserted into a compress device (90, FIG. 19, for example). The discrete nature of the modules 94 provide user's with the flexibility of inserting a desired number of modules and thereby affecting the device's overall flexibility, etc. For example, where the device 90 is to be applied and/or wrapped around smaller animal or body part, few modules 94 may be used, thereby leaving various wells 92 empty and increasing the flexibility and compressibility of the device, generally. Alternatively, each of the wells 92 may be provided with a module 94, thereby increasing the device's mass and associated ability to heat or cool a body part, but also potentially limiting the flexibility of the device.

In various embodiments, the modules 94 comprise a clear polyethylene thermoformed sheet of approximately 3 mm in thickness, and a top cover 104 that comprises a similar material and which is heat sealed or ultrasonically welded to the remainder of the module 94. In preferred embodiments, the modules 94 are filled with a quantity of hot/cold gel or similar liquid. For example, the modules 94 are contemplated as comprising benzoic acid, 4-hydroxy-methyl ester, hexadienoic acid, potassium salt, 2-propenoic acid, homopolymer, sodium salt, propanetriol, and water, and various combinations thereof.

Figure 20:
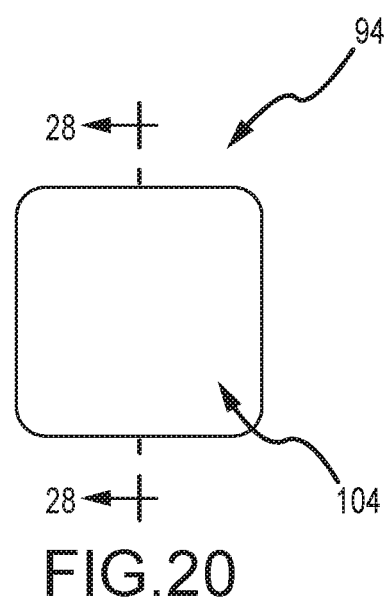
FIG. 20 is a top plan view of the device according to the embodiment of FIG. 19.
Figure 21:
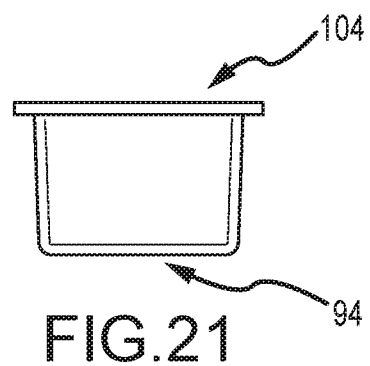
FIG. 21 is a side elevation view of the component according to the embodiment of FIG. 19.

FIG. 19 is a cross-sectional elevation view taken at line 28 of FIG. 20. FIG. 20 is a top plan view of the module 94 of FIG. 18. FIG. 21 is a side elevation view of the module 94 of FIG. 18. The module(s) are operable to be inserted into wells of a compress device (see 92 and 90 of FIG. 14, for example). The modules are sized and operable to be selectively inserted and removed from the wells.

Figure 22:
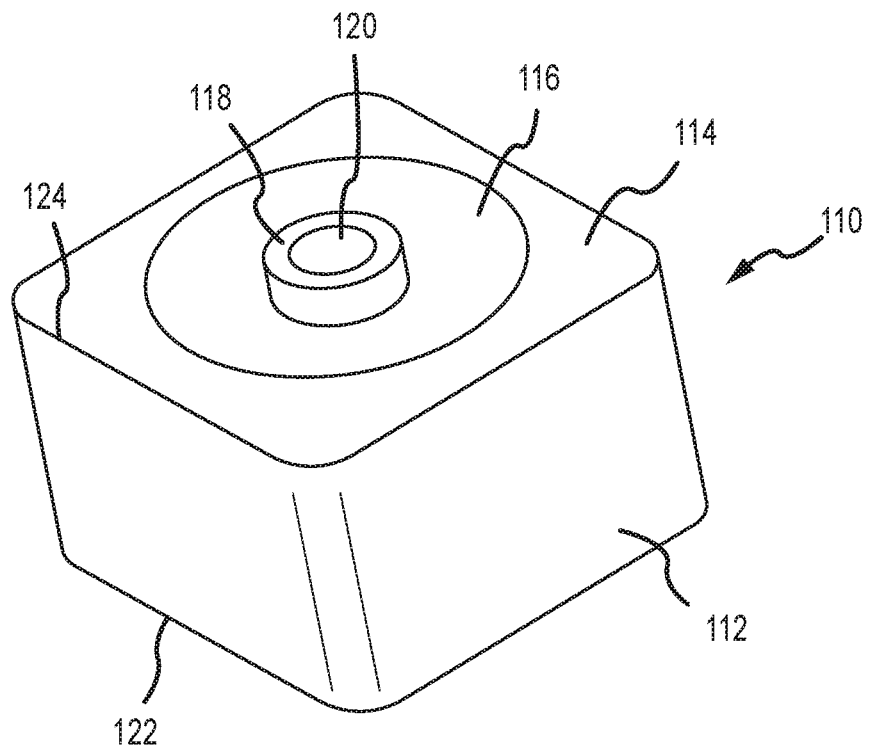
FIG. 22 is a perspective view of a component of a therapeutic device according to one embodiment of the present disclosure.

FIG. 22 is a perspective view of a module 110 according to one embodiment of the present disclosure. As shown, the module 110 comprises a substantially rectangular cube with a plurality of sidewalls 112 extending between an upper edge or lip 124 and a lower edge or lip 122. An upper surface 114 is provided as an opposing surface to a lower surface (not shown in FIG. 22). The upper surface 114 comprises a crater or depression 116 with an upstanding projection 118 that comprises an aperture 120 therein. In some embodiments, the depression 116 and the upstanding projection 118 are products of a molding process. In certain embodiments, the aperture 120 is provided as a fill and/or emptying port for fluids to be housed within the module 110. The module is operable to be provided within an array of well including, for example, those shown in FIG. 14. The lower lip 122 and/or upper lip 124 are operable to be provided in contact with an overhang of certain embodiments of the present disclosure (see, for example, 98 in FIG. 17). Embodiments of the present disclosure contemplate that a plurality of modules 110 are provided to collectively provide a therapeutic device for delivering heat or cooling/icing an animal patient.

Figure 23:
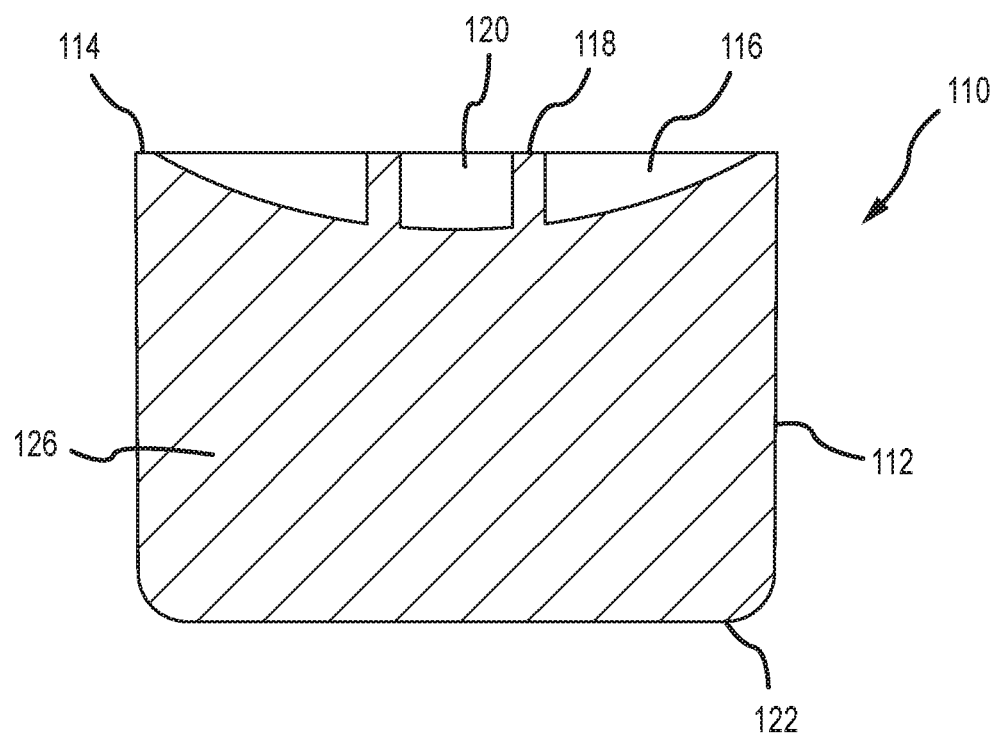
FIG. 23 is a cross-sectional elevation view of the component of FIG. 22.

FIG. 23 is a cross-sectional elevation view of the module 110 of FIG. 22. As shown, the module 110 comprises an internal volume 126 that is operable to receive and house a volume of fluid or other medium. In some embodiments, the fluid comprises a gel or water that may be frozen or heated numerous times. In some embodiments, the fluid comprises a contained fluid wherein egress of the fluid and ingress of additional fluid or material is prevented. The modules 110 of such embodiments may be selectively inserted and removed from a well, but the material within the internal volume of the module comprises a contained material.

While the present invention has been illustrated by description of preferred embodiments and while the illustrative versions have been described in considerable detail, it is not the intention of the inventors to restrict or in any way limit the scope of the appended claims to such detail. Additional advantages and modifications will readily appear to those skilled in the art upon reading this detailed description. Therefore, the invention, in its broader aspects, is not limited to these specific details, respective apparatus and methods, and illustrative examples shown and described. Accordingly, departures may be made from such details without departing from the spirit or scope of the inventor's general inventive concepts.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A therapeutic device for an animal comprising:
a flexible compress member having a plurality of wells;
wherein each of the plurality of wells comprises a plurality of sidewalls and a bottom portion;
wherein each of the plurality of wells comprises a first internal volume, an open area provided at an upper end of the well, and the upper end of the wells comprises an overhang extending at least partially around the open area and wherein the overhang provides a restriction at the upper end of the well;
a plurality of fluid-containing modules, wherein each of the plurality of fluid-containing modules is operable to be provided within the first internal volume of a well;
wherein each of the fluid-containing modules comprises a substantially rectangular cube having an upper end, a lower end, a plurality of sidewalls and a second internal volume, the second internal volume being less than the first internal volume;
a fluid provided within the second internal volume;
wherein the overhang comprises at least one of a flexible and an elastic component that is operable to selectively receive and at least partially secure a portion of a fluid-containing module by extending over the fluid-containing module; and
wherein the device is operable to act as a heating or cooling agent for an animal body part.

2. The therapeutic device of claim 1, wherein the device comprises silicone rubber.

3. The therapeutic device of claim 1, wherein the plurality of fluid-containing modules comprise silicone rubber.

4. The therapeutic device of claim 1, wherein the plurality of wells are arranged in a rectangular grid.

5. The therapeutic device of claim 1, further comprising a cover member.

6. The therapeutic device of claim 5, wherein the cover member extends along the upper end of the wells and comprises a seal for at least some of the plurality of wells.

7. The therapeutic device of claim 1, wherein the fluid-containing modules comprise sealed modules having a cover that is welded to upper edges of each module.

8. A therapeutic device for an animal comprising:
a flexible compress member having a plurality of wells;
wherein each of the plurality of wells comprises a plurality of sidewalls defining a first internal volume and an upper end of the wells comprises an overhang, the overhang extending substantially perpendicular to the sidewalls;
a plurality of fluid-containing modules, wherein each of the plurality of fluid-containing modules is operable to be provided within the first internal volume of a well;
wherein each of the fluid-containing modules comprise a second internal volume, the second internal volume being less than the first internal volume;
a fluid provided within the second internal volume;
wherein the overhang comprises at least one of a flexible and an elastic component that is operable to selectively receive and at least partially secure a portion of a fluid-containing module by extending over the fluid-containing module; and
wherein the device is operable to act as a heating or cooling agent for an animal body part.

9. The therapeutic device of claim 8, wherein the device comprises silicone rubber.

10. The therapeutic device of claim 8, wherein the plurality of fluid-containing modules comprise silicone rubber.

11. The therapeutic device of claim 8, wherein the plurality of wells are arranged in a rectangular grid.

12. The therapeutic device of claim 8, wherein at least some of the fluid-containing modules comprises substantially rectangular cubes.

13. The therapeutic device of claim 8, further comprising a cover member extending along the upper end of the wells and comprising a seal for at least some of the plurality of wells.

14. The therapeutic device of claim 8, wherein the fluid-containing modules comprise sealed modules.

15. A therapeutic device for an animal comprising:
a flexible member having a plurality of wells arranged in a rectangular grid;
wherein each of the plurality of wells comprises an overhang provided proximal to an upper end of each well and wherein the overhang provides a restriction at the upper end of the well, a plurality of sidewalls and a bottom portion;
wherein each of the plurality of wells comprises a first internal volume;
a plurality of fluid-containing modules, wherein each of the plurality of fluid-containing modules is operable to be provided within a well with the overhangs extending over at least a portion of the fluid containing modules;
wherein each of the fluid-containing modules comprises a sealed substantially rectangular cube having an upper end, a lower end, a plurality of sidewalls and a second internal volume, the second internal volume being less than the first internal volume;
a fluid provided within the second internal volume;
wherein the overhang comprises at least one of a flexible and an elastic component that is operable to selectively receive and at least partially secure a portion of a fluid-containing module;
wherein the device is operable to act as a heating or cooling agent for an animal body part.

16. The therapeutic device of claim 15, wherein the device comprises silicone rubber.

17. The therapeutic device of claim 15, wherein the plurality of fluid-containing modules comprise silicone rubber.

18. The therapeutic device of claim 15, wherein an upper end of the wells comprises at least one of an overhang and a constriction operable to at least partially secure a fluid-containing module.

19. The therapeutic device of claim 15, wherein the fluid-containing modules each comprise apertures operable to serve as fill ports for filling the fluid-containing modules.

20. The therapeutic device of claim 19, wherein the apertures are sealed after filling.

* * * * *